United States Patent [19]

Chasar

[11] 4,311,647
[45] Jan. 19, 1982

[54] PROCESS FOR PREPARATION OF (HYDROCARBONTHIO)OXAMIDES

[75] Inventor: Dwight W. Chasar, Northfield, Ohio

[73] Assignee: The B. F. Goodrich Company, Akron, Ohio

[21] Appl. No.: 135,598

[22] Filed: Mar. 31, 1980

[51] Int. Cl.³ .................... C07C 83/10; C07C 103/10
[52] U.S. Cl. ............................ 260/453 RW; 564/102
[58] Field of Search ...... 260/453 RW, 561 A, 562 N, 260/551 S; 564/102

[56] References Cited

U.S. PATENT DOCUMENTS 3,780,001  12/1973  Son .............................. 260/453 RW

OTHER PUBLICATIONS

Behforouz, et al., Journal Organic Chemistry, vol. 34, No. 1, p. 51, (1969).

*Primary Examiner*—John M. Ford
*Assistant Examiner*—Robert C. Whittenbaugh
*Attorney, Agent, or Firm*—J. Hughes Powell, Jr.

[57] ABSTRACT

(Hydrocarbonthio)oxamides are prepared by reacting hydrocarbon sulfenyl chloride with an oxamide in the presence of a tertiary amine catalyst in a water insoluble liquid fatty acid ester solvent.

6 Claims, No Drawings

PROCESS FOR PREPARATION OF (HYDROCARBONTHIO)OXAMIDES

BACKGROUND OF THE INVENTION

The preparation of use of (hydrocarbonthio)oxamides as vulcanization retarders is disclosed in U.S. Pat. No. 3,780,001. In accordance with this patent the (hydrocarbonthio)oxamides are prepared by reaction between a hydrocarbon sulfenyl chloride and an oxamide or derivative thereof in the presence of certain solvents including alkyl hydrocarbons such as heptane and hexane, halogenated alkyls such as carbon tetrachloride, trichloromethane, methylene chloride, trichloroethane, aromatic hydrocarbons such as benzene, toluene and chlorobenzene, or tetrahydrofuran, dioxane and dimethyl formamide, preferably tetrahydrofuran or dimethyl formamide. An improved process for the preparation and recovery of these (hydrocarbonthio)oxamides is desired.

SUMMARY OF THE INVENTION (Hydrocarbonthio)oxamides are prepared by reacting a hydrocarbon sulfenyl chloride with an oxamide in a water insoluble alkyl ester of a fatty acid solvent. Such esters, as ethyl acetate, have the advantage of being inexpensive and non-toxic, are water insoluble, and are poor solvents for the (hydrocarbonthio)oxamide, providing an improved method for recovery and purification of the (hydrocarbonthio)oxamide.

DETAILED DESCRIPTION

The (hydrocarbonthio)oxamides prepared in accordance with the improved process of this invention have the formula

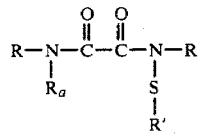

wherein R and $R_a$ are independently hydrogen, an alkyl, aryl, alkaryl, aralkyl or cycloalkyl radical containing 1 to 18 carbon atoms, or —SR′, and R′ is a hydrocarbon radical containing 1 to 24 carbon atoms. More preferably R′ is an alkyl, aryl, aralkyl, alkaryl or cycloalkyl radical containing 1 to 18 carbon atoms. Examples of such radicals are methyl, ethyl, propyl, isopropyl, butyl, isobutyl, hexyl, octyl, isooctyl, 2-ethylhexyl, decyl, dodecyl, t-dodecyl, tetradecyl, octadecyl, and the like; phenyl, naphthyl, anthracyl; tolyl, and other aralkyls such as p-ethylphenyl, o-, m-, p-butylphenyl, o-, m-, p-octylphenyl, 6-ethylnaphthyl, and the like; and cyclobutyl, cyclopentyl, cyclohexyl, cyclooctyl, and the like. Furthermore, the R, $R_a$ and R′ radicals can contain one or more substituents thereon such as —Cl, —Br, —$SO_2$, —$NO_2$, alkoxy and carboxy radicals containing 1 to 8 carbon atoms, and the like. More preferably, the substituents on R are electron-withdrawing groups such as —Cl, —$NO_2$, and —$SO_2$, whereas substituents on R′ are electron donating groups.

More preferably the (hydrocarbonthio)oxamides are of the formula

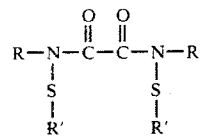

wherein R and R′ are defined as above. Examples of such compounds are N,N′-bis(methylthio)oxamide; N,N′-bis(ethylthio)N-butyl-oxamide; N,N′-bis(hexylthio)-N′-octyl-oxamide; N,N′-bis(decylthio)-N-isooctyloxamide; N,N′-bis(tetradecylthio)-N-dodecyl-oxamide; N-ethylthio-N′-hexylthio-oxamide; N-2-ethyl-hexylthio-N-butyl-N′-octylthio-oxamide; N,N′-bis(decylthio)-N,N′-bis(methyl)oxamide; N,N′-bis(isobutylthio)-N,N′-bis(octyl)-oxamide; N,N′-bis(phenylthio)oxamide; N,N′-bis(phenylthio)-N-hexyl-oxamide; N,N′-di(phenylthio)-N,N′-di(phenyl)oxamide; N,N′-bis(tolylthio)-N,N′-bis(phenyl)oxamide; N-phenylthio-N-phenyl-N′-methyl-N′-p-ethylphenylthiooxamide; N,N′-bis(benzylthio)-N,N′-bis(butyl)oxamide; N-naphthylthio-N′-isopropylthiooxamide; N,N′-bis(naphthylthio)-N,N′-bis(methyl)oxamide; N,N′-bis(methylthio)-N,N′-bis(tetradecyl)oxamide; N-hexylthio-N′-octylthio-N,N′-bis(phenyl)oxamide; N,N′-bis(isopropylthio)-N,N′-bis(phenyl)oxamide; N,N′-bis(t-dodecylthio)-N,N′bis(naphthyl)oxamide; N,N′-bis(phenylthio)-N,N′-bis(p-nitrophenyl)oxamide; N-cyclobutylthio-N′-isobutylthio-oxamide; N,N′-bis(cyclobutylthio)-N′-hexyloxamide; N-cyclopentylthio-N′-cyclohexylthio-N,N′-bis(phenyl)oxamide; N,N′-bis(cyclohexylthio)oxamide; N,N′-bis(cyclohexylthio)-N,N′-bis(phenyl)oxamide; N,N′-bis(cyclooctylthio)-N,N′-bis(p-chlorophenyl)oxamide; and the like.

More practically R is hydrogen or an aryl, aralkyl, or alkaryl radical containing 6 to 14 carbon atoms, and R′ is an alkyl or cycloalkyl radical containing 1 to 12 carbon atoms. Examples of such more preferred compounds are N,N′-bis(ethylthio)oxamide; N-butylthio-N′-hexylthio-oxamide; N,N′-bis(isopropylthio)-N,N′-bis(phenyl)oxamide; N,N′-bis(isooctylthio)-N-phenyl-oxamide; N-decylthio-N′-cyclobutylthio-oxamide; N,N′-bis(cyclopentylthio)-N,N′-bis(phenyl)oxamide; N,N′-bis(cyclohexylthio)oxamide; N,N′-bis(cyclohexylthio)-N,N′-bis(phenyl)oxamide; N-octylthio-N′-cyclooctylthio-N,N′-bis(naphthyl)oxamide, and the like.

The compounds are readily prepared by the reaction of a hydrocarbon sulfenyl chloride with oxamide or derivatives thereof. The reaction follows that employed by Behrorouz et al, Journal of Organic Chemistry, Vol. 34, page 51 (1969). The hydrocarbon sulfenyl chloride is prepared for example by reacting a hydrocarbon thiol of the formula R′—SH or a hydrocarbon disulfide of the formula R′—SS—R′ wherein R′ is defined as above, with halide gas as bromine, more preferably chlorine gas.

The hydrocarbon sulfenyl chloride is reacted with an oxamide of the formula

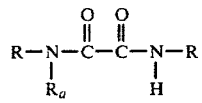

wherein R and $R_a$ are defined as above. Examples of such compounds are oxamide and N-, N,N′- and N,N,N'-derivatives of oxamide such as N-methyl, N-ethyl, N-isopropyl, N-butyl, N-hexyl, N-octyl, N-isooctyl, N-decyl, N-dodecyl, N-tetradecyl, N-phenyl, N-p-nitro-phenyl, N-p-methylphenyl, N-p-butylphenyl, N-naphthyl, N-6-ethyl-naphthyl, N-cyclohexyl, and the like; N,N'-di(methyl), N,N'-di(ethyl), N,N'-di(isopropyl), N,N'di(hexyl), N,N'-di(octyl), N,N'-di(dodecyl), N,N'-di(tetradecyl), N,N'-di(phenyl), N,N'-di(p-nitro-phenyl), N,N'-di(o-,m-p-chloro-phenyl), N,N'-di(p-ethyl-phenyl), N,N'-di(naphthyl), N,N'-di(6-ethyl-naphthyl), N,N-di(cyclohexyl) and the like; and N-methyl-N'-phenyl, N-hexyl-N'-octyl, N-phenyl-N'-naphthyl, and the like; and N,N-dimethyl-N'-ethyl, N-phenyl-N-methyl-N'-phenyl, and the like. More practically $R_a$ is hydrogen and R is hydrogen or an aryl, aralkyl or alkaryl radical containing 6 to about 14 carbon atoms wherein both R groups are the same. Examples of such are oxamide, N,N'-di(phenyl)oxamide (oxanilide), N,N'-di(4-methyl-phenyl)oxamide, N,N'-di(-naphthyl)oxamide, and the like.

The reaction between the hydrocarbon sulfenyl chloride and the oxamide may be conducted at a temperature from about $-10°$ C. to about 60° C., and more preferably from about 10° C. to about 40° C. About two moles of the sulfenyl chloride are used per mole of oxamide compound, though an excess of the chloride may be employed. Usually an organic liquid is used to aid the reaction. The liquids taught in the prior art are aromatic solvents such as benzene, toluene, and chlorobenzene, or tetrahydrofuran, dioxane, and dimethylformamide. Preferably tetrahydrofuran or dimethylformamide were used along with an alkyl or halogenated alkyl hydrocarbon.

According to U.S. Pat. No. 3,780,001, the cure retarder bis(cyclohexylthio)oxanilide may be prepared by reacting cyclohexylsulfenyl chloride with oxanilide in the presence of triethylamine in a mixed solvent such as tetrahydrofuran and a chlorinated hydrocarbon. Heptane or hexane may be added to this mixture at the end of the reaction and the bis(cyclohexylthio)oxanilide solid is filtered and washed with water to remove the triethylamine hydrochloride because the triethylamine hydrochloride cannot be washed out of the reaction mixture suspended in tetrahydrofuran with water. Thus the bis(cyclohexylthio)oxanilide must then be dried to remove the water, and separation of the mixed solvents for economical recycling is difficult and expensive.

When, according to U.S. Pat. No. 3,780,001, the reaction of cyclohexylsulfenyl chloride and oxanilide is conducted in tetrahydrofuran, at the end of the reaction there is obtained a thick slurry of triethylamine hydrochloride and bis(cyclohexylthio)oxanilide, with a substantial amount of the oxanilide dissolved in the tetrahydrofuran-heptane solution. Since tetrahydrofuran and water are miscible, water can not be used to extract the triethylamine hydrochloride. Thus another solvent such as heptane must be added in an attempt to obtain as much oxamide as possible out of solution, the oxamide filtered and reslurried with water to remove the triethylamine hydrochloride. In contrast, when ethyl acetate is employed the reaction mixture can be filtered to remove the reaction product since it is appreciably insoluble in ethyl acetate and the filter cake can be treated with water to extract the triethylamine hydrochloride. In a more preferred procedure, water can be added directly to the reaction mixture to extract the triethylamine hydrochloride which forms a lower layer under a top layer of ethyl acetate containing the insoluble oxanilide. The layers can be separated and the oxanilide filtered and dried immediately. In extracting the triethylamine hydrochloride with water any problem of hydrolysis of ethyl acetate is avoided by washing out the triethylamine hydrochloride with a water solution of sodium chloride. The bis(cyclohexylthio)oxanilide is readily recovered in greater than 90% yields of excellent purity.

The water insoluble esters useful as solvents in the process of this invention have the formula

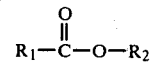

wherein $R_1$ is H, methyl, ethyl, propyl, isopropyl, n-butyl, isobutyl, sec-butyl, t-butyl, pentyl and phenyl; $R_2$ contains 1–4 carbon atoms and is methyl, ethyl, propyl, isopropyl, n-butyl, isobutyl, sec-butyl, t-butyl, pentyl and α-alkoxy ethyl wherein the alkoxy is methoxy or ethoxy. When $R_1$ is H, $R_2$ is preferably not methyl or ethyl; and when $R_1$ is methyl, $R_2$ preferably is not methyl since these materials are more water soluble and do not provide as convenient a recovery procedure for the (hydrocarbonthio)oxamides. While ethyl acetate, propyl acetate and butyl acetate represent a useful group of water insoluble solvents, ethyl acetate is preferred.

The reaction can be catalyzed by tertiary amines such as trimethylamine, triethylamine, N,N'-dimethylaniline, and the like, or an organic lithium compound such as n-butyl lithium can be used. Reaction time is from about 1 to about 4 hours. If the (hydrocarbonthio)oxamides are not soluble in the liquid mix, they can be isolated by filtration. The compounds can be purified by washing with water and/or recrystallizing them from hexane or benzene. The compounds were characterized by their infra-red (IR) and nuclear magnetic resonance (NMR) spectra, their melting point, by carbon, hydrogen, nitrogen, and sulfur analysis (C,H,N,S content), and by their mass spectra to determine molecular weight.

The (hydrocarbonthio)oxamides are employed in the range from about 0.02 part to about 5 parts by weight per hundred parts by weight of polymer. More preferably, they are used in from about 0.1 to about 3 parts by weight. The compounds are highly effective vulcanization retarders, often delaying the onset of cure 200% or more when used at the level of about 1 part by weight. Over the range from 0.5 to 5 parts by weight, they bloom much less than comparably effective retarders.

The (hydrocarbonthio)oxamides are useful vulcanization retarders with a wide range of sulfur and nitrogen-based accelerator compounds. The accelerators may be used alone or in combination with each other. Elemental sulfur is typically employed with these accelerators in levels from about 0.1 to about 10 parts by weight per hundred parts of polymer. The novel vulcanization retarders are used to delay the cure of sulfur-vulcanizable polymers such as natural rubber, cis-polyisoprenes, cis-polybutadienes, polybutadienes, butadiene-acrylonitrile polymers, polychloroprenes, and styrene-butadiene rubbers. The retarders can be used with a full range of compounding ingredients. This includes activators such as metal oxides, fillers such as the carbon blacks, plasticizers and extenders such as dialkyl and diaryl organic acids, antioxidants, antiozonants, and stabilizers, and other ingredients such as pigments, tackifiers, flame retardants, fungicides, and the like.

The vulcanization retarders, accelerators, sulfur, and other compounding ingredients are admixed with the polymer using conventional equipment such as two-roll mills and internal mixing equipment such as banburys, extruders, and Brabender mixers. Standard mixing equipment and addition techniques are employed.

EXAMPLES

This example sets forth a procedure for the preparation of bis(cyclohexylthio)oxanilide in accordance with the improved process of this invention. To a 250 ml reactor equipped with a stirrer, thermometer and nitrogen inlet, there is added 14.4 grams (0.06 mol) of oxanilide, 16.2 grams (0.16 mol) of triethylamine and 150 ml of ethyl acetate. While this mixture is stirred rapidly at room temperature, cool (−5° to −10° C.) cyclohexylsulfenyl chloride is slowly added in amount of 21.08 grams (0.139 mol). The reaction temperature should be controlled to below about 40° C. After this addition has been completed the reactor is stirred for about two hours. The resulting bis(cyclohexylthio)oxanilide in a yield of 93% may be recovered by any of the following methods.

(I) The reaction mixture is cooled to −10° C., is washed with two successive 150 ml portions of 0° C. saturated sodium chloride solution to remove the triethylamine hydrochloride. The ethyl acetate containing the reaction product is filtered and the filter cake washed with cooled ethyl acetate and dried in a vacuum.

(II) The reaction mixture is cooled to −10° C. and filtered by a vacuum. The filter cake is mixed with 150 ml of water, filtered, and washed again and filtered. The filter cake is then washed with cooled ethyl acetate and vacuum dried.

(III) The reaction mixture is centrifuged and the filter cake is washed directly in the centrifuge with a saturated aqueous sodium chloride solution or saturated sodium bicarbonate solution to remove the triethylamine hydrochloride and the filter cake is then dried.

When this reaction was repeated with chloroform, n-butyl ether, bis(2-methoxyethyl) ether) and 2-ethoxyethyl acetate as solvents, very poor yields were obtained and difficulty with work up was encountered. Ethyl acetate is relatively inexpensive and immiscible with water and is one of the least toxic solvents known. An unexpected advantage in the use of ethyl acetate over tetrahydrofuran is that the bis(cyclohexylthio)oxanilide has a very low solubility in ethyl acetate while it has substantial solubility in tetrahydrofuran. Thus the use of ethyl acetate is more amenable to variation in work up procedures to recover the reaction product.

I claim:

1. In a method of preparing (hydrocarbonthio) oxamides of the formula

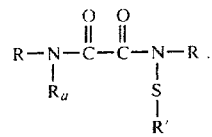

wherein R and $R_a$ are hydrogen or are selected from the group consisting of alkyl, aryl, aralkyl, alkaryl, cycloalkyl radicals containing 1 to 18 carbon atoms and —SR′, and R′ is a hydrocarbon radical containing 1 to 24 carbon atoms by reacting together a hydrocarbon sulfenyl chloride with an oxamide of the formula

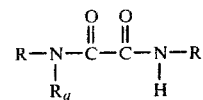

in the presence of a tertiary amine and an organic solvent, improvement comprising selecting said solvent from liquid water insoluble aliphatic esters having the formula

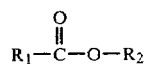

wherein $R_1$ is H, methyl, ethyl, propyl, isopropyl, n-butyl, isobutyl, sec-butyl, t-butyl, pentyl and phenyl; $R_2$ is methyl, ethyl, propyl, isopropyl, n-butyl, iso-butyl, sec-butyl, t-butyl, pentyl and α-alkoxy ethyl wherein the alkoxy is methoxy or ethoxy.

2. A method of claim 1 wherein R is hydrogen or an aryl, aralkyl, or alkaryl radical containing 6 to 14 carbon atoms, $R_a$ is —SR′, and R′ is selected from the group consisting of alkyl, aryl, aralkyl, alkaryl, and cycloalkyl radicals containing 1 to 18 carbon atoms, $R_1$ is H and $R_2$ contains 1 to 4 carbon atoms.

3. A method of claim 2 wherein said ester solvent is ethyl acetate.

4. A method of claim 3 wherein $R_a$ is hydrogen and R is hydrogen or aryl, aralkyl or alkaryl radicals containing 6 to 14 carbon atoms wherein both R groups are the same.

5. A method of claim 4 wherein the hydrocarbon sulfenyl chloride is cyclohexyl sulfenyl chloride and the oxamide is oxanilide.

6. A method of claim 5 wherein said reaction is conducted at a temperature of from about −10° C. to about 60° C., with a molar excess of the sulfenyl chloride, the tertiary amine is triethylamine and the resulting hydrocarbon bis(cyclohexylthio)oxanilide is recovered by washing the reaction mixture with saturated sodium chloride solution, separating the ethyl acetate containing the reaction product and filtering to recover the bis(cyclohexylthio)oxanilide.

* * * * *